US00PP31811P2

(12) United States Plant Patent

Klemm et al.

(10) Patent No.: US PP31,811 P2

(45) Date of Patent: May 26, 2020

(54) ***PELARGONIUM* PLANT NAMED 'KLEPZ18546'**

(50) Latin Name: *Pelargonium zonale*
Varietal Denomination: KLEPZ18546

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,839

(22) Filed: Jun. 17, 2019

(51) Int. Cl.
*A01H 5/02* (2018.01)
*A01H 6/42* (2018.01)

(52) U.S. Cl.
USPC ..... Plt./328

(58) Field of Classification Search
USPC ..... Plt./324, 325, 328
See application file for complete search history.

*Primary Examiner* — Susan McCormick Ewoldt

(74) *Attorney, Agent, or Firm* — Barbara Campbell; Cochran Freund & Young LLC

(57) ABSTRACT

A new *pelargonium* plant particularly distinguished by neon-pink flowers with white centers, and bushy and round plant habit with medium vigor, is disclosed.

1 Drawing Sheet

Genus and species: *Pelargonium zonale.*
Variety denomination: 'KLEPZ18546'.

CROSS-REFERENCE TO RELATED APPLICATIONS

A Swiss Plant Breeders Rights Application was filed on May 31, 2018, Application No. 18-3220 and a Community Plant Variety Rights application was filed on Jul. 19, 2018, File No. 2018/1823. 'KLEPZ18546' has not been made publicly available more than one year prior to the filing date of the instant application.

BACKGROUND OF THE NEW PLANT

The present invention comprises a new and distinct variety of *pelargonium*, botanically known as *Pelargonium zonale* and hereinafter referred to by the variety name 'KLEPZ18546'. 'KLEPZ18546' originated from a hand-pollination in September 2011 in Stuttgart, Germany between the female *pelargonium* variety 'KLEPZ08245', also commercially known as SUNRISE 'Elaine' (unpatented) and the male *pelargonium* variety 'KLEPZ07203', also commercially known as SUNRISE 'Boomerang' (unpatented).

Seeds from the hand-pollination were obtained. The seeds were sown and plants were grown for evaluation. A single plant was selected in June 2012 and subsequently named 'KLEPZ18546'. In September 2012 'KLEPZ18546' was first vegetatively propagated by vegetative cuttings. 'KLEPZ18546' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Neon-pink flowers with white centers; and
2. A bushy and round plant habit with medium vigor.

DESCRIPTION OF THE PHOTOGRAPH

This new *pelargonium* plant is illustrated by the accompanying photograph which shows an overall view of the plant. The photograph is of an approximately 6-month-old plant grown outdoors in Remseck, Germany, in September 2018. The colors shown are as true as can be reasonably obtained by conventional photographic procedures.

DESCRIPTION OF THE NEW VARIETY

The following detailed descriptions set forth the distinctive characteristics of 'KLEPZ18546'. The data which define these characteristics were collected from asexual reproductions carried out in Stuttgart, Germany. Data was collected on 19-week-old plants in Stuttgart, Germany under greenhouse conditions in April 2019. Color references are to The R.H.S. Colour Chart of The Royal Horticultural Society of London (R.H.S.), 6$^{th}$ edition (2015).

Classification:
*Family.*—Geraniaceae.
*Botanical.*—*Pelargonium zonale.*
*Common.*—*Pelargonium.*
*Designation.*—'KLEPZ18546'.

Parentage:
*Female parent.*—'KLEPZ08245' (unpatented).
*Male parent.*—'KLEPZ07203' (unpatented).

Plant:
*Form.*—Bushy and round.
*Habit.*—Upright.
*Vigor.*—Medium.
*Height (from top of soil).*—20 cm.
*Width (horizontal plant diameter).*—30 cm.
*Natural flowering season.*—April to October.
*Propagation type.*—Vegetative cuttings.
*Time to produce a finished flowering plant.*—3 months.
*Time to initiate and develop roots.*—4 weeks.
*Root description.*—Fine, moderate density, RHS 199C.

Stems:
*Quantity of stems per plant.*—4 to 5.
*Color.*—RHS 144B.
*Surface texture.*—Sparsely pubescent.
*Stem form.*—Round.
*Diameter.*—0.7 cm.
*Length.*—5 to 6 cm.
*Internode length.*—1 to 1.5 cm.
*Anthocyanin.*—Absent.

Leaves:
*Arrangement.*—Alternate.
*Shape.*—Reniform.
*Apex.*—Round.
*Base.*—Slightly open.
*Margin.*—Crenate.
*Surface texture (both surfaces).*—Sparsely pubescent.
*Length.*—5 cm.
*Width.*—8 cm.
*Color.*—Upper surface: RHS 137B. Lower surface: RHS 138A.
*Zonation.*—Present.
*Zone conspicuousness.*—Very weak.
*Zone position.*—Towards margin.
*Zone width.*—Broad.
*Zonation color.*—RHS 137A.
*Petiole.*—Length: 5 cm to 6 cm. Diameter: 0.2 cm. Color: RHS 144A. Strength: Moderate.
*Venation pattern.*—Palmate.
*Venation color.*—Upper surface: RHS 144B. Lower surface: RHS 144C.

Inflorescence:
*Lastingness of flowers on the plant.*—6 to 8 days.
*Umbels.*—Quantity of umbels per plant: 11. Length: 7 cm. Diameter: 12 cm.
*Individual florets of the umbel.*—Quantity of florets per umbel: 28 to 30. Depth: 2 cm. Diameter: 4.5 cm.
*Fragrance.*—Absent.

Flower buds:
*Cluster shape.*—Round.
*Cluster size.*—Length: 1.5 cm. Width: 2 cm.
*Surface texture.*—Sparsely pubescent.
*Bud.*—Height: 0.8 cm. Width: 0.7 cm. Shape: Round. Apex: Acute. Base: Obtuse. Margin: Entire. Color: RHS 144C.

Petals:
*Quantity per flower.*—8 to 9.
*Shape.*—Spatulate.
*Apex.*—Round.
*Base.*—Obtuse.
*Margin.*—Entire.
*Length.*—2.5 cm.
*Width.*—3 cm.
*Surface texture (both surfaces).*—Smooth.
*Color of lobes (both upper and lower lobes).*—Upper surface: RHS N66A and NN155D towards base. Lower surface: RHS N66C and NN155D towards base.

Petaloids:
*Quantity per flower.*—2.
*Shape.*—Like petals but smaller, some mal-shaped and twisted.
*Apex.*—Round.
*Base.*—Obtuse.
*Margin.*—Entire.
*Length.*—1.7 cm.
*Width.*—0.4 cm.
*Surface texture (both surfaces).*—Smooth.
*Color.*—Upper surface: RHS N66B and NN155D towards base. Lower surface: RHS N66C and NN155D towards base.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Sparsely pubescent.
*Color.*—Upper surface: RHS 144B. Lower surface: RHS 144A.
*Length.*—1 cm.
*Width.*—0 cm.

Pedicel:
*Length.*—3 cm.
*Diameter.*—0.1 cm.
*Color.*—RHS 144A.
*Surface texture.*—Sparsely pubescent.
*Strength.*—Moderate.

Peduncle:
*Length.*—13 cm.
*Diameter.*—0.5 cm.
*Color.*—RHS 144A.
*Texture.*—Moderately pubescent.
*Strength.*—Moderate.

Reproductive organs:
*Stamens.*—Quantity per flower: 10. Anther length: 0.8 cm. Filament length: 0.2 cm. Filament color: RHS 63C. Pollen amount: Moderate. Pollen color: RHS 31A.
*Pistils.*—Number: 1. Stigma color: RHS 63A. Style length: 0.6 cm. Style color: RHS 144B. Ovary arrangement: Central. Ovary color: RHS 144A. Ovary diameter: 0.2 cm. Ovary length: 0.2 cm.

Fruit and seed set: None observed.
Disease and pest/insect resistance: None observed.

COMPARISON WITH PARENTAL LINES AND KNOWN VARIETY

'KLEPZ18546' is distinguished from its parents as described in Table 1:

TABLE 1

Comparison with Parental Lines

| Characteristic | 'KLEPZ18546' | Female parent 'KLEPZ08245' | Male Parent 'KLEPZ07203' |
|---|---|---|---|
| Flower color | Neon-pink with white center | Purple-pink with white center | Light-pink with a purple red eye |
| Vigor | Medium | Medium | Strong |

'KLEPZ18546' can be compared to the commercial variety SUNRISE 'Hurricane', also known as 'KLEIRRO' (U.S. Plant Pat. No. 9,216). Differences between the two varieties are described in Table 2:

TABLE 2

Comparison with Similar Variety

| Characteristic | 'KLEPZ18546' | 'KLEIRRO' |
|---|---|---|
| Flower color | Neon-pink with white center | Purple-pink with white center |

We claim:

1. A new and distinct variety of *pelargonium* plant named 'KLEPZ18546' as illustrated and described herein.

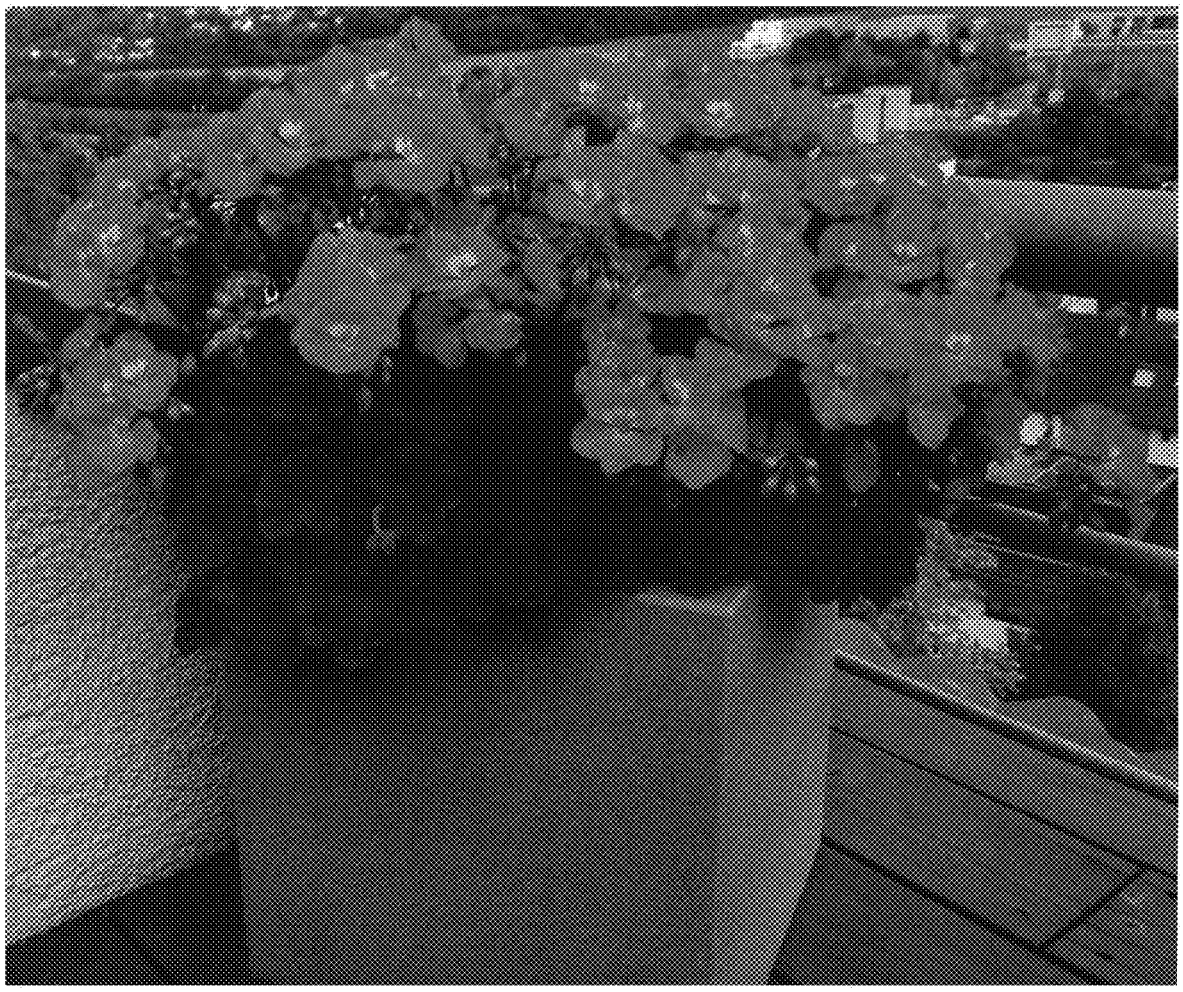

* * * * *